United States Patent [19]

Steffel

[11] Patent Number: 5,083,306
[45] Date of Patent: Jan. 21, 1992

[54] APPARATUS FOR THE MULTI-LATERAL X-RAY TESTING OF AUTOMOTIVE TIRES

[75] Inventor: Horst Steffel, Gross Grönau, Fed. Rep. of Germany

[73] Assignee: Spezialmaschinenbau Steffel GmbH & Co. KG, Ratzeburg, Fed. Rep. of Germany

[21] Appl. No.: 265,072

[22] Filed: Oct. 31, 1988

[30] Foreign Application Priority Data

Nov. 2, 1987 [DE] Fed. Rep. of Germany ....... 3737159

[51] Int. Cl.$^5$ ............................................. G01N 23/02
[52] U.S. Cl. ........................................ 378/61; 378/62; 378/207
[58] Field of Search ................. 378/58, 61, 62, 147, 378/19, 207; 250/370.15

[56] References Cited

U.S. PATENT DOCUMENTS

| | | | |
|---|---|---|---|
| 3,766,387 | 10/1973 | Heffan et al. | 378/207 |
| 3,873,837 | 3/1975 | Palermo, Jr. | 378/61 |
| 4,352,020 | 9/1982 | Horiba et al. | 378/207 |
| 4,371,976 | 2/1983 | Wagner | 378/147 |
| 4,456,826 | 6/1984 | Forster | 378/19 |
| 4,725,734 | 2/1988 | Nishiki | 378/147 |
| 4,759,047 | 7/1988 | Donges et al. | 378/99 |
| 4,831,639 | 5/1989 | Harke | 378/19 |

FOREIGN PATENT DOCUMENTS

| | | |
|---|---|---|
| 2231792 | 1/1974 | Fed. Rep. of Germany ........ 378/61 |
| DE2239003 | 2/1974 | Fed. Rep. of Germany . |
| DE2262982 | 6/1974 | Fed. Rep. of Germany . |
| DE3530938 | 3/1987 | Fed. Rep. of Germany . |

Primary Examiner—Craig E. Church
Attorney, Agent, or Firm—Faegre & Benson

[57] ABSTRACT

An apparatus for the multi-lateral X-ray testing of rotatably supported automotive tires during their rotation comprising an omni-directional X-ray tube located within the space encircled by the tire adjacent its opened inner side, the radiation emanating from said tube transilluminating the side walls and the tire tread from inward outwardly, further comprising receiving means defined by three linear diode arrangements of light-sensitive diodes which are approximately located parallel to the diameter or the axis of said tire, respectively, scanning means being associated with the diode arrangements scanning the diodes with a predetermined scanning frequency, the output signals of the diodes being transmitted to a storage means and finally comprising image reproduction means consisting of individual picture elements for the generation of an image line per scanning sequence for the diode arrangement.

13 Claims, 3 Drawing Sheets

APPARATUS FOR THE MULTI-LATERAL X-RAY TESTING OF AUTOMOTIVE TIRES

The invention refers to an apparatus for the multi-lateral X-ray testing of rotatably supported automotive tires during at least one revolution of the tire.

An X-ray testing apparatus is known from the German patent specification 22 39 003 where an X-ray tube is located within the tire in the medial plane thereof to penetrate the tread of the tire. Two X-ray tubes are located outwardly of the tire which in operational position are symmetrically oriented with respect to the medial plane of the tire so that all X-ray tubes with their focuses lying in a common plane which extends perpendicularly to the central plane of the tire, said common plane registering with the optical axis of the first of the X-ray tubes. Fluorescent screens are associated with the outer side of the tread and the side walls, the radiation from the fluorescent screens associated with the tire side walls is transmitted to an X-ray camera through a mirror system while a further camera receives a radiation from the fluorescent screen associated with the tread. The cameras are connected to monitors so that an operator can recognize possible failures through the rotation of the tire.

With the known apparatus, a double penetration of tire portions can only be avoided if the outwardly located X-ray tubes radiate into the tire under a relatively acute angle. Such an oblique penetration aggravates the recognition of failures. If this disadvantage is to be avoided double penetrations of both side walls or a side wall portion and the bead, respectively, cannot be prevented. If the upper bead is to be reproduced, it has to be projected through the lower side wall (if regarded from the X-ray tube); on the other hand, if the lower surface is to be reproduced, the radiation has to penetrate the upper bead. The shadows generated thereby make it difficult to achieve a satisfactory failure recognition, above all, if plastic cord is used. The double images have a different scale and move with different speed on the screen of the monitor. A particular problem exists with the testing of tires having plastic cord. The reason resides in the small contrast between rubber and plastic material. A sufficient contrast can only be achieved if the radiation energy is not too large. The known apparatus has to have large distances between the X-ray tubes and the fluorescent screens. The tubes, thus, have to have a large power; as is known, the intensity reduces with the square of the distance from the source. The described double penetration causes a power reduction of about 100 per cent. The double penetration of a tire wall which is necessary to test the other wall generates a scattered radiation which aggravates the failure recognition.

If fluorescent screens or similar receiving means are used the complete apparatus is immobile. A penetration of the side walls under an angle of about 90° requires a double penetration of the side walls. As outlined above, a relatively acute penetration angle has to be accepted on the other side. Both methods enable only a restricted observation of the tire structure. Distortions and overlapping portions occur in the reproduced areas which aggravate the recognition of failures. An immobile arrangement has the further disadvantage that each tire size is reproduced under another scale. The operator therefore has to transpose the scale in order to carry out a satisfactory failure recognition or failure association, respectively. Therefore, the requirements to the operators are very high.

A testing apparatus for tires is known from the German patent specification 22 62 982 using a so-called omnidirectional X-ray tube which in one plane has a radiation angle of more than 180° and in a plane perpendicular thereto a radiation angle of 20° to 40°. Picture-receiving units are associated with the tread and the side walls of the tire, the means being defined by X-ray image multipliers, a fluorescent screen with associated video camera or by an X-ray sensitive video camera. The output signals are transmitted to an image reproduction device, e.g. a monitor. By means of such a testing apparatus only small tire speeds are performed since due to the small radiation angle of 20° to 40° only a very small zone is penetrated contemporarily.

The object of the invention is to create an apparatus for the multi lateral X-ray testing of automotive tires which is simply structured and which allows a high tire speed and thus a high production rate and which is particularly suited for the testing of tires having plastic cord.

With the apparatus according to the invention, an omnidirectional X-ray tube is used. Such X-ray tubes are known. They have a radiation angle up to 300° along one plane. Perpendicularly thereto, they have normally a radiation angle up to 40°. Usual testing apparatuses for automotive tires use X-ray tubes having a conical radiation angle of about 40°. Through the use of a single X-ray tube, the expense for the testing apparatus according to the invention is reduced with respect to conventional apparatuses. Further, the testing apparatus according to the invention is more economical because X-ray tubes are wearable parts which have to be replaced from time to time.

With the apparatus according to the invention the X-ray tube is located adjacent the open inner side of the tires, preferably at least partially within the tire. By this, an approximately perpendicular penetration of all tire portions to be tested is achieved and thus a distortion-free reproduction on the reproduction device, e.g. a monitor.

The apparatus according to the invention uses three linear arrangements of light-sensitive diodes which arrangements or lines are located parallel to the diameter and the axis, respectively, of the tire. Such diode arrangements or diode lines are known. They are scanned in series. The width of the line is very small, e.g. 0.5 mm. The output signals of the diodes are transmitted to a memory or storage from which they are transmitted to an image screen. The control of the storage means is such that a predetermined number of lines contemporarily appear on the image screen, the lines on the screen corresponding to a predetermined scanning incrementally pass from top to bottom, the increments corresponding to the line distance. By this, a predetermined portion of the tire to be tested appears on the image screen, the size of the portion depending on the scanning speed and on the rotational speed of the tire.

In an embodiment of the invention, it is provided that the distance of the diode lines from to the tire can be varied. By means of the displaceable diode lines, the distance from the outer side of the side walls or the tire tread can be held constantly and thus also the image scale. The same image scale is used for each tire size whereby a considerable facilitation for the operator is achieved.

With the apparatus according to the invention the X-ray source can be brought very near to the portions to be tested. Thus, it can be operated with lower energy which as already mentioned is favourable for the contrast between rubber and plastic material. A further advantage of the apparatus according to the invention consists in the overall dimensional reduction of the complete X-ray arrangement. Therefore, not only the structural expense is reduced, but also the space requirements.

From the German patent specification 35 30 938 it has become known for the testing of luggage, e.g. in airports, to use diode lines. A single X-ray source, however, not an omni-directional X-ray source, is X-raying the luggage diode lines being located adjacent and above the passage through which the luggage is conveyed. The resolution which can be achieved by the known diode lines may be sufficient for the luggage examination, however, does not suffice the testing of the structure of automotive tires. According to an embodiment of the invention at least three diodes per 2 mm length of the diode lines are provided. In the apparatus according to the invention the diodes are extraordinarily closely arranged with one another. Further, a very high scanning speed is selected, at least 10 m/sec., preferably 1 pixel per second. With such a diode arrangement and scanning speed a resolution is obtained by which very small failures can be recognized.

The speed at which the reproduced tire runs along the respective diode lines due to the linearity of the diode line and the circular form of the tire and the distance of a diode line from the tire is not equal to the circumferential speed but larger in any case. Therefore, the distance is selected as small as possible, and the scanning frequency which has to be adapted to the circumferential speed of the tire has to be corrected by a factor which corresponds to the distance.

The circumferential speed normally is determined by the operator who is free to change the speed, e.g. to reduce it in order to carry out a more thorough examination. If no corresponding measures are undertaken, the image scale would also change. If the mentioned distance is not small enough and/or the circumferential speed and the scanning frequency are too different a satisfactory image reproduction cannot be achieved. A further embodiment of the invention provides for a speed sensing device which senses the circumferential speed of the tire. The scanning speed is automatically adapted to the circumferential speed. The circumferential speed of a tire along its side walls is normally depending on the radius of the respective side wall portion. As to the diode lines associated with the side walls, a medium circumferential speed is selected in order to achieve a uniform image scale.

Preferably, driving means are used to displace the diode arrangements, e.g. frequency-controlled electrical motors. By this, a very fine and vibrationless displacement of the diode arrangement can be achieved. To obtain a constant distance of the diode arrangements from the tire to be tested, an embodiment of the invention provides for a test position feeler for each diode arrangement which is connected to a control device for the driving means. As soon as the position feeler is transmitting a signal to the control device, the associated driving means is cut off. The position feeler for example can be formed by an optical light barrier. Also two light barriers can be provided in order to reduce the displacement speed if the first light barrier is reached in order to bring the diode arrangement thereafter in the final testing position under creeping velocity.

The thickness of the tire to be tested is quite different. The intensity of the X-rays impinging on the diodes depends upon the thickness of the tire. In order to achieve an approximately equal brightness on the image reproduction device according to an embodiment of the invention the voltage of the X-ray tube is varied in dependence of the thickness. It needs some problems to always measure the thickness of a tire. The width and/or the diameter of the tires form criteria for the thickness so that it is sufficient to measure these values and to vary the voltage at the omni-directional X-ray tube in dependence of these values.

The image of the tire generated on the image reproduction device has to have the same brightness if possible. This meets some problems. The light- or X-ray-sensitive diodes individually change their sensitivity. Further, the individual diodes are subjected to different radiation in dependence of the distance from the X-ray source if the diode lines are displaced to adjust the predetermined distance from the tire. The intensity of the radiation of an omni-directional X-ray tube is not constant through its radiation angle. Therefore, the intensity of the X-rays impinging a diode of the diode line also changes with its angular relation with respect to the X-ray tube. Therefore it is necessary to carry out a calibration from time to time. Due to different distances from the X-ray source and the different thickness of the material penetrated (the bead of a tire is particularly thick while the side walls adjacent the tread are relatively thin), the diodes are subjected to different radiation intensity. Correspondingly, the output signals of the diodes have different values. In order to achieve a uniform brightness on the image screen the signals introduced in the storage have to have approximately equal values. With this method the diode arrangements associated with the tire tread and the side walls, respectively, are brought into a predetermined calibration position which is completely different from the testing position. Preferably, at first a socalled dark calibration is carried out wherein the X-ray source is switched off. This calibration serves only to adjust the diodes to an equal sensitivity. Alternatively, the output signals of the diodes can be regulated that approximately equal values are transmitted to the storage means. Thereafter, the so-called bright calibration is carried out. With this method for example an absorption member is brought ahead of the switched on X-ray source which is approximately of the same material as that of the tire and has a thickness approximately that of the tire having the smallest wall thickness. As mentioned, the radiation intensity at the individual diodes changes when the diode arrangements are displaced. Such displacement is appropriate or necessary, respectively, in order to adjust the constant distance from the tire. In other words, the distances of the diodes from the X-ray source and their angular relation to the X-ray source change with the size of a tire. For this, it appears necessary to calibrate the diodes for each tire size or each distance separately. This would lead to a great expense. In the invention it has been recognized that for the diode arrangements a calibration position is existing which significantly deviates from the individual testing positions and in which the diodes can be satisfactorily calibrated, the fact that the distance and the angular relations of the diodes as well as the thickness of the testing material to be penetrated remarkably influence the response of the diodes to the impinging X-rays assisting in compensating for failures upon calibration. So for example those diodes which in the testing position are illuminated through a thicker wall portion of the tire are illuminated with a weaker radiation in the calibration position so that the diodes are made automatically more sensitive etc. The calibration position, therefore, is selected such that the individual diodes are illuminated by the X-rays such as if a tire would be penetrated and the diodes would be located in the testing position.

With a conventional testing apparatus, the problem exists to make a uniform image of thin and thick portions of the tire wall. In case the radiation intensity is large in order to sufficiently reproduce thicker portions the thinner portions are overradiated and thus are less visible. Vice versa a satisfactory reproduction of the thinner portions lead to a weak image of the thicker portions. With the aid of the calibration method according to the invention, these problems are avoided. In the calibration position wherein the diode arrangements have a significantly larger distance from the X-ray source, the diodes are calibrated such that for all different test positions the tire can be satisfactorily transilluminated and reproduced. The suitable calibration position for the diode arrangements can be found by experiments.

By means of the calibration method, the brightness differences and the different distances from the X-ray source due to the different thickness of the tire wall can be compensated, and the operator can observe an approximately uniformly bright and clear image.

The invention be explained hereinafter along drawings.

Figure 1:
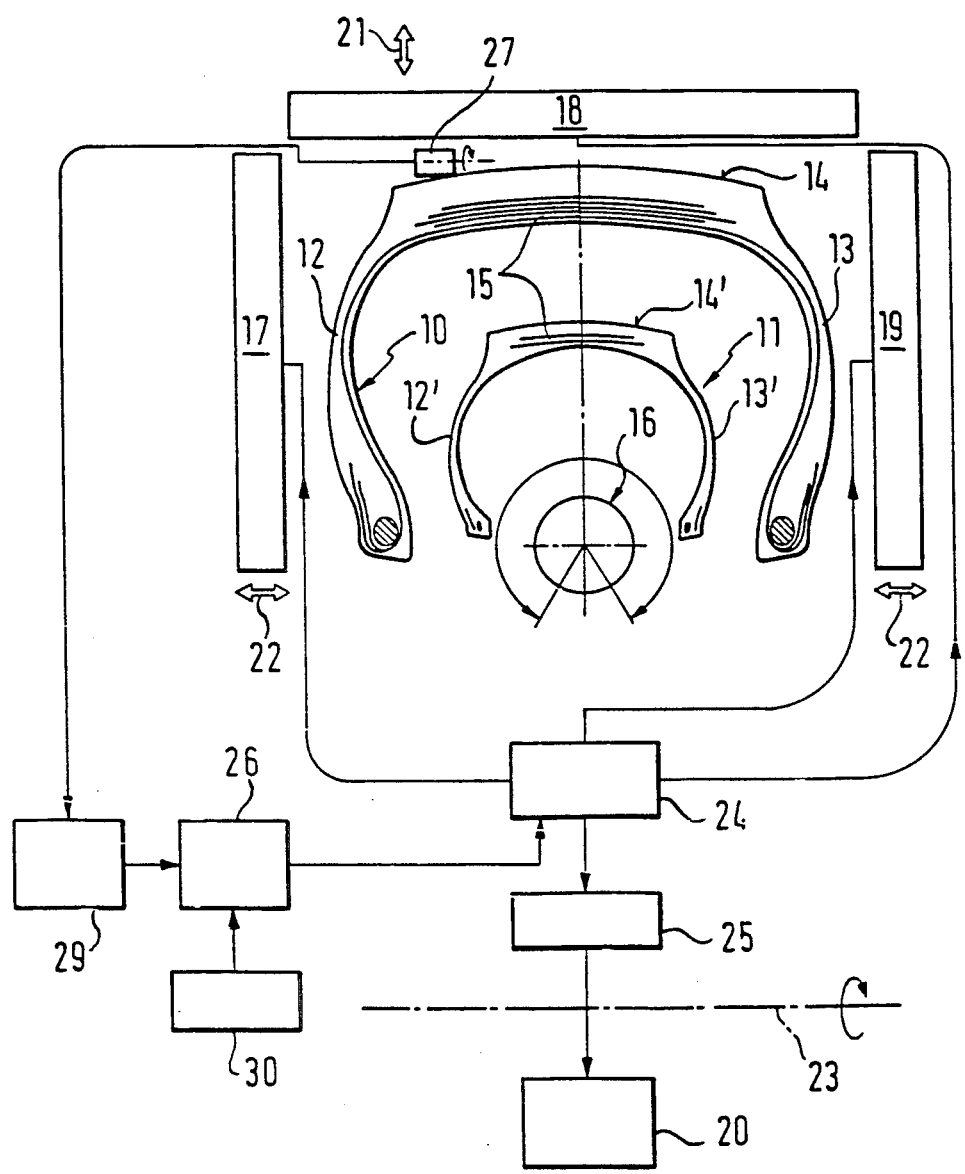
FIG. 1 shows the testing apparatus according to the invention including a speed-depending scan control.

In FIG. 1 two different large tires 10, 11 are shown in cross section. Their side walls 12, 13 and 12', 13', respectively, and their tread 14 and 14', respectively, are provided with plastic cord 15. The tire 10, 11 is rotatably supported as known per se about a vertical axis (in the drawings this axis is in the drawing plane and horizontally extending). The tire is rotated by rotating means (not shown) about its axis 23, the circumferential speed is controlled by the operator and can be changed. The respective structural measures therefore are not shown; they belong to prior art. Also the protection provisions for X-ray testing apparatuses are not shown.

As can be seen in FIG. 1 an omni-directional X-ray tube 16 is located at the entrance of the tire 10 or 11, respectively. In the radial plane with respect to the tire (in this case in the drawing plane), the omni-directional X-ray tube 16 has a radiation angle of about 300°. In the radial plane all portions of the tire are transilluminated by the radiation of tube 16, the penetration angle amounting to approximately 90°. It is understood that the X-ray tube 16 can be displaced towards the interior of the tire 10, 11 or more outwardly. In a plane perpendicular to the radial plane, the omni-directional X-ray tube 16 has a radiation angle approximately of 40°.

Diode arrangements or diode lines 17, 18, 19 are located on the outer sides of the outer walls 12, 13 and 12', 13', respectively and the outer side of the tread 14 or 14', respectively. These diode lines are only diagrammatically indicated. Each diode line 17 and 19 includes a linear arrangement of individual light- or X-ray-sensitive diodes, the diode line of the arrangements 17 and 19 extend approximately parallel to the diameter and the diode line of the arrangement 18 extends approximately parallel to the axis of the tire. The diodes are cyclically scanned by a scanner 24, the scanned signals are stored in a storage 25 in a manner as known per se, a plurality of scans contemporarily appears on a reproduction device 20, e.g. an image screen. The reproduction device 20 is also diagrammatically indicated. It consists of three individual image screens (not shown).

The scanning speed of the scanner 24 is controlled by a clock generator 26. A speed sensor 27, e.g. a tachometer roll is associated with the tread 14, 14, of the tire 10, 11. The output signal is transmitted to a control device 29 which in turn is connected to the clock generator 26. The scanning speed of the scanner 24 is varied in dependence of the speed of the tire 10, 11 in order to obtain an equal image scale under a predetermined distance of the diode arrangements 17 to 19 from the tire. The control device 29 calculates a mean value for the speed of the side walls of the tire. The scanning speed for the tread on one side and of the side walls 12, 12, on the other side are quite different. If the distance from the tire is changed, the scanning frequency has to be changed also. This is indicated by block 30.

Figure 3:
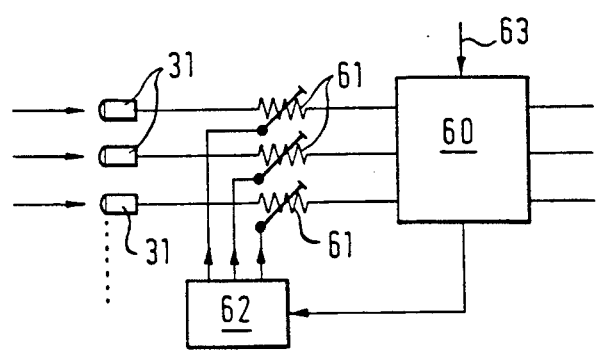
FIG. 3 shows extremely diagrammatical some diodes of a diode arrangement and the control of their output signals as well.

The diodes of the diode lines 17 to 19 are arranged closely together. In FIG. 3, three X-ray-sensitive diodes 31 are illustrated. Their distance of their axes is 0.4 to 0.5 mm. For example, the diode arrangements 17 to 19 include 1024 diodes. The image screen of the monitor 20 has a corresponding number of picture elements per line. In order to achieve a satisfactory resolution, the scanning speed is selected such that it is for example 10 m/sec., preferably 1 pixel per second.

The diode arrangements 17 to 19 form a U-shape and are supported by a common support member not shown, the support member being displaceable along double arrow 21 in a machine frame also not shown. The diode arrangements 17 and 19 each are supported by a second support member (not shown) which is adapted to be displaced parallel to itself on the first support member as is indicated by double arrows 22. The diode arrangement 18 can be also made displaceable along its longitudinal axis in order to achieve a centering with respect to the tire or to test very broad treads by two revolutions, approximately a half of the tread is tested upon one revolution. By the described displacement means, a uniform and equal distance from the outer side of the tire 10 or 11, respectively, and from the tread can be adjusted in order to achieve a uniform image scale. The adjusting means are frequency-controlled electrical motors 35, 36 and 37 which are controlled by a control device 38 and which effect on a toothed rod 42, 43, 44 through pinions 39, 40, 41 in order to displace the diode arrangements 17, 18 and 19 and the associated support members, respectively. Motor 36 displaces the first support member and thus all diode arrangements 17, 18 and 19.

Independent of the tire size the diode arrangements 17 to 19 should have the same distance from the tire. To this purpose, each diode arrangement 17 to 19 is provided with a light barrier consisting of a transmitter 45 and a receiver 46. The receivers 46 are connected to the control device 38. If upon displacement of the diode arrangements 17 to 19 toward the tire the light beam between transmitter 45 and receiver 46 is interrupted, a respective signal is transmitted to control device 38 which now stops the driving means 35 to 37.

Figure 2:
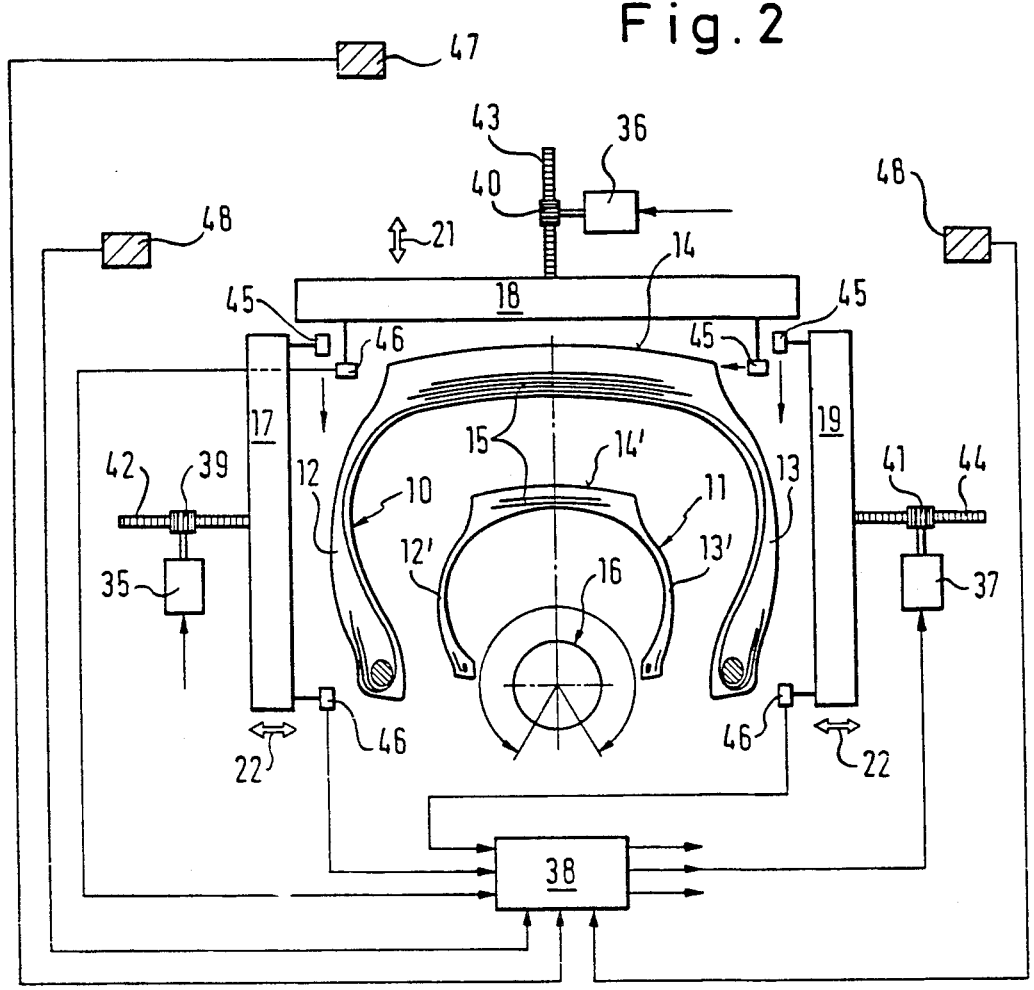
FIG. 2 shows a similar illustration as FIG. 1 indicating the displacement of the diode arrangements.

FIG. 2 shows also position sensors 47 and 48 which are also connected to the control device 38. They serve for the automatical displacement of the diode arrangements 17 to 19 in a calibration position. It is understood that the position sensors 47, 489 also can be associated with the toothed rods 42, 43 or 44 (the calibration method is dealt with more below).

A temperature regulating means is associated with the diode arrangements 17 to 19 which keeps the diodes at a predetermined temperature. By this, the time intervals after which a bright and dark calibration has to be carried out for the diodes can be increased. This favourably effects the production rate.

Slot-like diaphragms can be associated with the diode arrangements 17 to 19 which are for example made of plumbum (not shown). They form a barrier for scattered radiation coming from outward and prevent the electronic elements and components from being affected by the X-rays.

Figure 4:
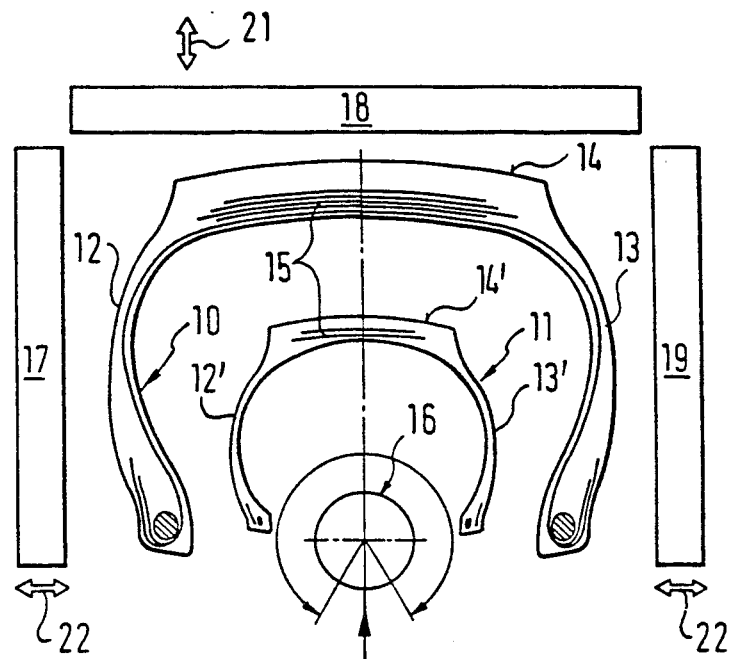
FIG. 4 shows a similar illustration as FIGS. 1 and 2 including a control of the voltage of the X-ray source.

FIG. 4 shows the diode arrangements 17 to 19 of FIGS. 1 and 2. The driving means are omitted. The omni-directional X-ray tube 16 is connected to a control circuit 50 adapted to change the voltage at tube 16. The control circuit 50 in turn is controlled by the control device 51 which is connected to optical sensing means 52 and 53. These sensing means 52, 53 can also be structured by lines of light-sensitive diodes. Their purpose is to measure the width and the diameter of a tire 54. Accordingly, a light source 55 and 56, respectively, is associated with the sensing means 52, 53. The width and the diameter of a tire allows an estimation of its wall thickness. The voltage of tube 16 is changed accordingly, i.e. is increased with a larger diameter or a larger width and decreased with a smaller diameter and a smaller width.

Figure 5:
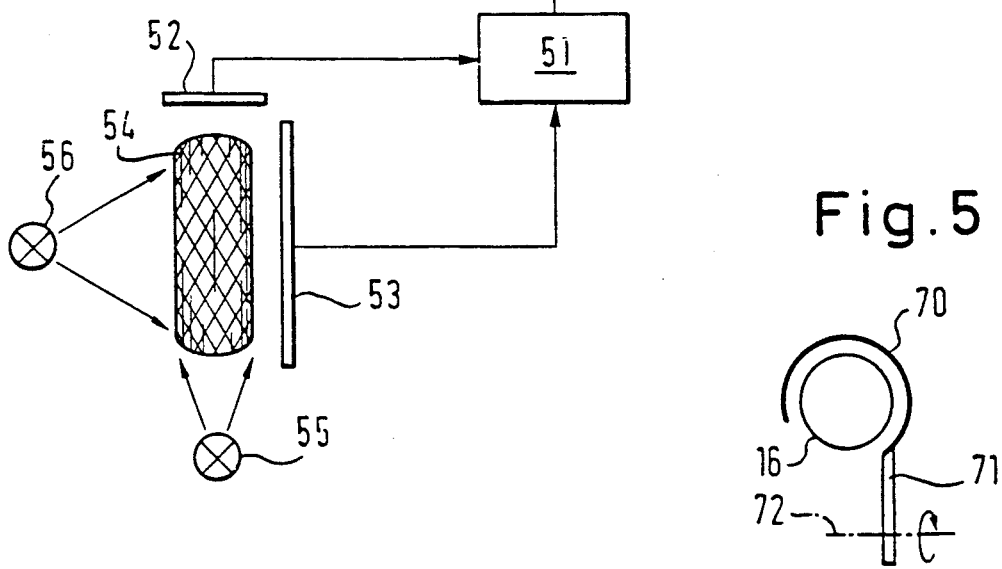
FIG. 5 shows a detail for the testing apparatus of the FIGS. 1, 2 and 4.

In order to achieve an approximately uniform brightness on the image screen, it is necessary to modify the sensitivity of the diodes 31 or the value of signals coming from the diodes. To this purpose, for example, the output lines of diodes 31 are connected to control means 60. Varying elements 61 are connected in the lines between diodes 31 and the control device 60 in order to change the sensitivity of diodes 31 or the output signals, respectively. The varying elements 61 are controlled by the control device 62. The control device 60 provides that the signals transmitted to the storage 25 have approximately the same or constant output (FIG. 1). Of course, the contrasts which are a result of the tire structure must be made visible. However, the illumination on the screen should be approximately uniform for all tire portions. The control device 60 is operated only during the calibration process. This is indicated by input arrow 63. During the calibration process, no tire is between the diode arrangements 17 to 19. The control device 38 displaces the diode arrangements 17 to 19 through the driving means 35 to 37 into the calibration position. First, the diode arrangement 18 is brought to its calibration position which is automatically determined by position sensor 47. Position sensor 48 automatically determines the position of the diode arrangements 17 to 19 if these are to be calibrated. The relative position of the diode arrangements 17 to 19 with respect to the X-ray tube 16 is essential. The diode arrangements are displaced into a position which is normally not attained in the test operation. In the calibrating position for example both diodes which in the test operation are subjected to intensive X-rays due to their position because they receive the radiation through a thinner wall portion of the tire have a relatively small distance from the X-ray source or a favourable angular position, respectively, so that they are illuminated with relatively high intensity. The adjustment on uniform sensitivity effects that these diodes are made less sensitive. Thus, a situation is simulated as occurs in the test operation, i.e. an illumination of the diodes with X-rays which depends upon the distance of the diodes from the X-ray source and which is different with respect to the material penetrated. Independent from the described calibration position, the dark calibration can be carried out. This is only to adjust the diodes to an equal sensitivity. This occur when the tube 16 is switched off. By means of the control device 60 shown in FIG. 3, the output signals of the diodes 31 are adjusted to equal sensitivity. By this, the normally changing individual sensitivity of the diodes 31 can be compensated. Upon bright calibration, as shown in FIG. 5, an annular member 70 is brought in front of the X-ray tube 16. Member 70 is attached to an arm 71 which can be rotated about an axis 72 by an actuation means not shown. The member 70 consists of the same material as the tires 10, 11 and has a thickness which corresponds to the thickness of the thinnest tire to be tested. The X-rays 16 first penetrate the test member 70 before they illuminate the diodes of the diode arrangements 17 to 19. By means of the calibration process described approximately a uniform brightness is achieved on the screens of the monitor 70 (FIG. 1).

I claim:

1. A testing device for multi-lateral X-ray testing of an automotive tire supported for rotation about an axis, comprising an omni-directional X-ray tube means for emitting radiation, the radiation penetrating a first and second side wall and a thread of the tire, receiving means located exterior of the side walls and the tread for receiving said radiation penetrating the tire, said receiving means being connected to optical indication means, said X-ray tube means being located in a space encircled by the tire adjacent an open inner side of the tire, said radiation emanating from said X-ray tube penetrating said side walls and said tread from the interior outwardly, said receiving means including a first and second linear diode line of light-sensitive diodes said first line aligned parallel to the axis of rotation of the tire and said second line aligned parallel to a diameter of the tire, scanning means connected to said diode lines for scanning the diodes with a predetermined scanning frequency and for transmitting an output signal of said diodes to a storage means, and image generating means having a plurality of picture elements for generating a scanning line per scanning sequence of said diode lines, and wherein the scanning frequency of said scanning means can be changes, wherein further a speed-sensing means is provided sensing a rotational speed of the tire, input means for generating a distance signal corresponding to the distance of the diode lines from the outer side of the tire, the scanning frequency being varied in response to the sensed rotational speed.

2. The apparatus according to claim 1, wherein the omnidirectional X-ray tube is at least partially located within the tire.

3. The apparatus according to claim 1 or 2 wherein said first diode line and said second diode line are each supported for displacement with respect to a distance from the tire.

4. The apparatus according to claim 1, wherein said first line parallel to the axis is located on a first support member coupled with a first driving means, said first support member being displaceable along a displacement axis approximately perpendicularly to the tread, said second line is associated with a first side wall of the tire and is located on a second support member coupled to a second driving means, said second support member being displaceable perpendicular to said displacement axis by said second driving means.

5. The apparatus according to claim 1, wherein temperatureregulating means are associated with said diode lines to maintain the diodes at a predetermined temperature.

6. The apparatus according to claim 1, wherein at least three diodes per 2 mm length of the diode lines are arranged in each of said diode lines.

7. The apparatus according to claim 1, wherein said scanning means scans said diodes with a scanning speed of at least 10 m/sec.

8. The apparatus according to claim 4, wherein each driving means comprises a frequency-controlled electrical motor.

9. The apparatus according to claim 4, further comprising a control device and a plurality of test position sensors, with one sensor being associated with each of said diode lines and wherein said control device transmits a switch-off signal to each of said driving means for positioning the respective diode line associated with that driving means when the diode line is a predetermined distance from the tire.

10. The apparatus according to claim 4, wherein each driving means comprises a DC motor.

11. A testing device for multi-lateral X-ray testing of an automotive tire supported for rotation about an axis, comprising an omni-directional X-ray tube means for emitting radiation, the radiation penetrating a first and second side wall and a tread of the tire, receiving means located exterior of the side walls and the tread for receiving said radiation penetrating the tire, said receiving means being connected to optical indication means, said X-ray tube means being located in a space encircled by the tire adjacent an open inner side of the tire, said radiation emanating from said X-ray tube penetrating said side walls and said tread outwardly, said receiving means including a first and second linear diode line of light-sensitive diodes said first line aligned parallel to the axis of rotation of the tire, and said second line aligned parallel a diameter of the tire, scanning means connected to said diode lines for scanning the diodes with a predetermined scanning frequency and for transmitting an output signal of said diodes to a storage means, and image generating means having a plurality of picture elements for generating a scanning line per scanning sequence of said diode lines, and further comprising a size measuring device to measure the width and the diameter of the tire to be tested, and a voltage control means is connected to said X-ray tube for applying a voltage to said X-ray tube, the size measuring device transmitting a size signal to said voltage control means for varying the voltage applied to said X-ray tube in response to the value of the size signal.

12. A method for calibrating the testing of tires comprising the steps of:
(a) progressively displacing a diode arrangement associated with a tire tread and a diode arrangement associated with each of a tire side wall in predetermined respective calibration positions relative to an omni-directional X-ray tube different from a testing position,
(b) illuminating all the diode arrangements with a plurality of X-rays from said X-ray tube through a calibration member effecting an absorption of said X-rays, the material of said calibration member approximately corresponding to that of the tire and having a thickness corresponding to the thickness of a thinnest tire to be tested, wherein each diode arrangement has a plurality of diodes, and each diode is adjusted with respect to sensitivity such that an output signal from said each diode is approximately independent of distance from and angular relation to the X-ray tube, and
(c) selecting a calibrating position such that the X-rays impinging on the diode arrangements as if a tire would be in a testing position relative to said diode arrangements; and wherein a driving means and a second position sensor is respectively associated with each diode arrangement and is connected to said control device, and further wherein said control device generates a switch-off signal for the respective driving means when the associated diode arrangement has reached said respective calibration position.

13. The method of claim 12 further comprising the additional step of moving said calibration member selectively in front of said tube or away from said tube into a rest position, respectively, by actuation means for selectively moving said calibaration member with respect to said tube.

* * * * *